US005553154A

United States Patent [19]

Tamamura et al.

[11] Patent Number: 5,553,154

[45] Date of Patent: Sep. 3, 1996

[54] VEHICLE INTERNAL NOISE REDUCTION SYSTEM AND THE METHOD THEREOF

[75] Inventors: Manpei Tamamura, Ohta; Hiroshi Iidaka, Tokyo; Eiji Shibata, Oura, all of Japan

[73] Assignee: Fuji Jukogyo Kabushiki Kaisha, Tokyo, Japan

[21] Appl. No.: 357,118

[22] Filed: Dec. 16, 1994

[30] Foreign Application Priority Data

Dec. 28, 1993 [JP] Japan .................................... 5-334709

[51] Int. Cl.[6] ............................ A61F 11/06; H03B 29/00

[52] U.S. Cl. ................................................ 381/71; 381/94

[58] Field of Search ............................ 381/71, 94, 73.1, 381/86

[56] References Cited

U.S. PATENT DOCUMENTS

| | | | |
|---|---|---|---|
| 5,251,262 | 10/1993 | Suzuki et al. | 381/71 |
| 5,319,715 | 6/1994 | Nagami et al. | 381/71 |
| 5,416,844 | 5/1995 | Nakaji et al. | 381/71 |
| 5,426,703 | 6/1995 | Hamabe et al. | 381/71 |
| 5,426,704 | 6/1995 | Tamamura et al. | 381/71 |

*Primary Examiner*—Forester W. Isen
*Assistant Examiner*—Xu Mei
*Attorney, Agent, or Firm*—Beveridge, DeGrandi, Weilacher & Young, L.L.P.

[57] ABSTRACT

Pulses synchronized with the period of the noise are generated and inputted to the adaptive filter. On the other hand, the tap number of the delay line of the adaptive filter is terminated at a tap number which is equal to the interval of the inputted pulse, whereby the number of times for calculation at the adaptive filter can be substantially reduced. Furthermore, in case where the tap number of the adaptive filter is changed according to the change of the period of the noise sound, the filter coefficient for cutting the high frequency domain is convoluted into the tap value of the adaptive filter, whereby noises caused by the change of the tap number can be eliminated even when the tap number of the adaptive filter is changed.

4 Claims, 8 Drawing Sheets

VEHICLE INTERNAL NOISE REDUCTION SYSTEM AND THE METHOD THEREOF

BACKGROUND OF THE INVENTION

1. Technical Field

The present invention relates to a noise reduction system and the method thereof for a passenger compartment of automotive vehicle by positively generating a sound from a sound source to cancel the vehicle internal noise and more specifically relates to a noise reduction system to reduce a noise produced periodically.

2. Related Prior Arts

There have been proposed several techniques for reducing a noise sound in the passenger compartment by producing a canceling sound having the same amplitude as the noise sound and a reversed phase thereto from a sound source disposed in the passenger compartment.

Among these prior arts, Japanese Patent Application Laid Open No. Toku-Kai-Hei 3-178846 discloses the following technique:

Referring now to FIGS. 9 to 11, FIG. 9 is a block diagram of the noise reduction system according to the prior art. FIG. 10 is a block diagram showing the adaptive filter section and the tap value updating section according to the prior art. Further, FIG. 11 is a block diagram showing the the prior art. In FIG. 9, numeral 10 indicates a noise source, numeral 11 a pick-up circuit, numerals 12 and 16 analogue-to-digital (A/D) converters, numeral digital-to-analogue (D/A) converter, numeral 14 a speaker, numeral 7 an adaptive filter, numeral 8 a transmission characteristic compensation section and numeral 9 a tap value updating section.

A microphone 15 is disposed in a position where a noise is to be reduced. The adaptive filter 7 corrects an error signal e (t), namely a difference between a noise signal picked up by the pick-up circuit 11 and a noise inputted into the microphone 15 and the corrected signal is transmitted from the speaker 14. Then the signal which reaches the microphone 15 generates a signal having the same amplitude as and a reversed phase to the noise sound from the noise source 10.

As details will be described hereinafter in FIG. 10, the adaptive filter 7 is a digital filter composed of delay lines with tap. Namely, by inputting an output signal from the pick-up circuit to the adaptive filter 7, the transmission characteristic of filter can be determined such that a sound pressure and a wave form are reversed at the position of the microphone 15. This adaptation is performed at the tap value updating section 9.

Since compensating transmission characteristics are affected by a time lag, a band restriction or the like while a signal is generated from the adaptive filter 7 and reaches the microphone 15 through the D/A converter 13 and the speaker 14, the transmission characteristic compensation section 8 act as compensating them and sending a compensated signal having the same amplitude as and the reversed phase to the signal from the noise source 10 to the tap value updating section 9.

These transmission characteristics can also be composed of digital filters of delay lines with tap. FIG. 11 is a schematic diagram showing a composition of the transmission characteristic compensation section 8. Numerals 80-1 to 80-J are delay elements for controlling a timing of sampling pulse inputted to the A/D converters 12 and 16. Further, 81-0 to 81-J are tap values by which an output value of the delay element is multiplied and then the multiplied output value is outputted.

Now where the output value of the A/D converter 12 is x (n) at $t=t_n$ and x (n+1) at $t=t_{n+1}$, further where $<i=1, 3>\Sigma x_i=x_1+x_2+x_3$ is expressed, the compensation signal C (n) from the transmission characteristic compensation section 8 is expressed as $$C(n)=<i=0, J>\Sigma x(n-i)C_i \quad (1)$$

The adaptive filter 7 comprises delay elements 70-1 to 70-Z, tap values 71-0 to 71-Z and an adder 72, as shown in FIG. 10, The delay element 70 controls a timing of sampling pulse inputted to the A/D converter 12.

Consequently, the output y (n) from the adaptive filter is expressed as:

$$y(n)=<i=0,Z>\Sigma x(n-i)W_i(n) \quad (2)$$

y (n) is converted into an analogue signal in the D/A converter 13 and transmitted to the speaker 14.

The tap values $W_O$ (n) to $W_z$ (n) of the adaptive filter 7 are updated at the tap value updating section 9 each time the sampling pulse is generated. As illustrated in FIG. 10, the tap value updating section 9 comprises multipliers 90, 91 and 92 and an adder 93.

First, in the delay element 90 the output signal C(n) from the transmission characteristic compensation section 8 inputted and transmitted after the signal is delayed by a time equal to the sampling pulse interval. Further, in the multiplier the output e(t) from the microphone 15 is multiplied by α after being converted into a digital value in the A/D converter 16. This value α is predetermined according to a loop characteristic of the adaptive control system.

Next, the updated W (n+1) is calculated with respect to each of tap values of the adaptive filter 7. The explanation will be made about the case where the tap value $W_0$ (n) of the tap 71-0 is updated to $W_O$ (n+1) in order to make explanation easier. In the multiplier 92-0 the output of the multiplier 91 is multiplied by the output value C (n) of the transmission characteristic compensation section 8. the adder 93-0 the output value of the multiplier 92-0 is subtracted from the tap value $W_0$ (n) at $t=t_n$ and the result of the subtraction is updated into a tap value $W_0$ (n+1) at the next $t=t_{n+1}$, That is to say:

$$W_0(n+1)=W_0(n)-\alpha C(n)e(n) \quad (3)$$

Further, other tap value Wi will be updated as follows;

$$W_i(n+1)=W_i(n)-\alpha C(n-i)e(n) \quad (4)$$

As described hereinbefore, in the noise reduction system according to the prior art by means of passing a noise signal picked up from the noise source through the adaptive filter a sound having the same amplitude as and a reversed phase to a noise sound is generated from the speaker 14 to reduce the noise in the vicinity of the microphone.

Accordingly, it is necessary to carry out equal number of multiplications in the adaptive filter and equal number of additions to tap numbers in the tap value updating section.

When these multiplications and additions are carried out by independent multipliers and adders, a construction of the system becomes very complicated, therefore commonly these calculations are performed by a processor. However, even when using a processor, in order to carry out equal number of multiplications and additions to tap numbers at an interval of sampling pulse an expensive high speed processor is needed.

SUMMARY OF THE INVENTION

In view of the foregoing disadvantage, it is an object of the present invention to provide a vehicle internal noise reduction system having a very simple construction.

Before describing means constituting the present invention, the principle of the invention will be explained hereinafter:

In the prior art, the signal to be inputted to the adaptive filter is picked up from the noise source whose spectrum is similar to a noise sound to be inputted to the microphone. However, it is not necessary to input a signal which has a similar spectrum to the noise sound. If the spectrum of the noise sound is contained therein, any signal can be used. In other words, if the spectrum of the noise sound is contained, it is possible to make the same waveform as the noise sound by changing the filter characteristic.

Further, with respect to the cyclic (periodical) noise sound it is possible to obtain an appropriate filter characteristic by equalizing the total delay time of delay lines with a period of the noise sound. That is to say, since the noise sound is cyclic, it is possible that a response to the noise signal of one cycle is divided by the period of the noise sound and the divided responses are superposed each other. Namely, a principle of superposition can be established here.

The present invention is based upon this principle. In the prior art the calculation of y (n) shown in the formula (2) must be conducted from i=0 to i=Z, on the other hand, in the case of the present invention, the same calculation may be conducted up to i=I (No. "I"th tap) where the delay quantity is equal to the period of the noise sound, Further, also with respect to the updating of tap value, the calculation of $W_i$ shown in the formula (4) may be conducted from i=0 to i=I.

Further, by means of inputting a pulse syncronized with the period of the noise sound from the noise source to the adaptive filter, the spectrum of the pulse can be broadened enough to contain the whole spectrum of the noise sound. Further, when the amplitude x of the pulse is normalized into "1", the formula (2)

$$y(n)=<i=K_1,\ K_2>\Sigma W_i(n) \qquad (5)$$

where $K_1$ and $K_2$ indicate numbers of the delay element by which it shows that pulses exist from No, $K_1$ delay element to No. $K_2$ delay element.

As recognized tn the above formula, since the calculation is carried out only by the addition process, it can be simplified. Further, when the period of the noise sound is changed, namely the tap number I of the adaptive filter is changed, noises generated with the change of tap number can be removed by giving a filter characteristic for cutting a high frequency domain to the adaptive filter.

Disclosed is a vehicle internal noise reduction system comprising:

- synchronizing pulse generating means for generating a pulse synchronized with a period of the noise to generate the signal from the adaptive filter and the signal for compensating the transmission characteristic;
- pulse interval detecting means for detecting an interval of the pulse generated from the synchronizing pulse generating means;
- tap number switching means responsive to the interval from the synchronizing pulse generating means for switching a tap number of the adaptive filter to a cut-off tap number equal to a delay quantity of a delay line with tap for the adaptive filter so as to shorten calculation times by the adaptive filter;
- filter coefficients recording means for recording a filter coefficient to cut a high frequency domain contained in the output signal from the adaptive filter;
- convolution means for convoluting the filter coefficient into the tap value of the adaptive filter; and
- driver means for driving the convolution means when the period of the noise is changed.

In the vehicle internal noise reduction system thus constituted, first the synchronizing pulse generating means generates a pulse synchronized with the period of the noise and inputs the pulse to the transmission characteristic compensation means. In the pulse interval detecting means, the interval of the pulse generated in the synchronizing pulse generating means is detected.

Next, the tap number switching means truncate and switch a tap number when the delay quantity of the delay line with tap becomes equal to the pulse interval detected by the pulse interval detecting means. Further, when it is detected that the interval of the noise has been changed, the driver means command the convolution means to read out the filter coefficient for cutting off the high frequency domain recorded in the filter coefficient recording means and to convolute it into the tap value of the adaptive filter, whereby noises generated at the change of the tap number are eliminated.

As described above, since the noise reduction system according to the present invention is constituted such that a pulse synchronized with the period of the noise is generated, the pulse is inputted to the adaptive filter and a tap number of the delay line is truncated at the tap number equal to the period of the inputted pulse, the number of calculations of the adaptive filter can be reduced substantially and the construction of the system can be simplified. Further, when the tap number of the adaptive filter is changed according to the change of the period of the noise, since the filter coefficient for cutting of the high frequency domain is convoluted into the tap value, noises generated by the change of the tap number can be eliminated when the tap number of the adaptive filter is changed.

DETAILED DESCRIPTION OF PREFERRED EMBODIMENTS

Figure 1:
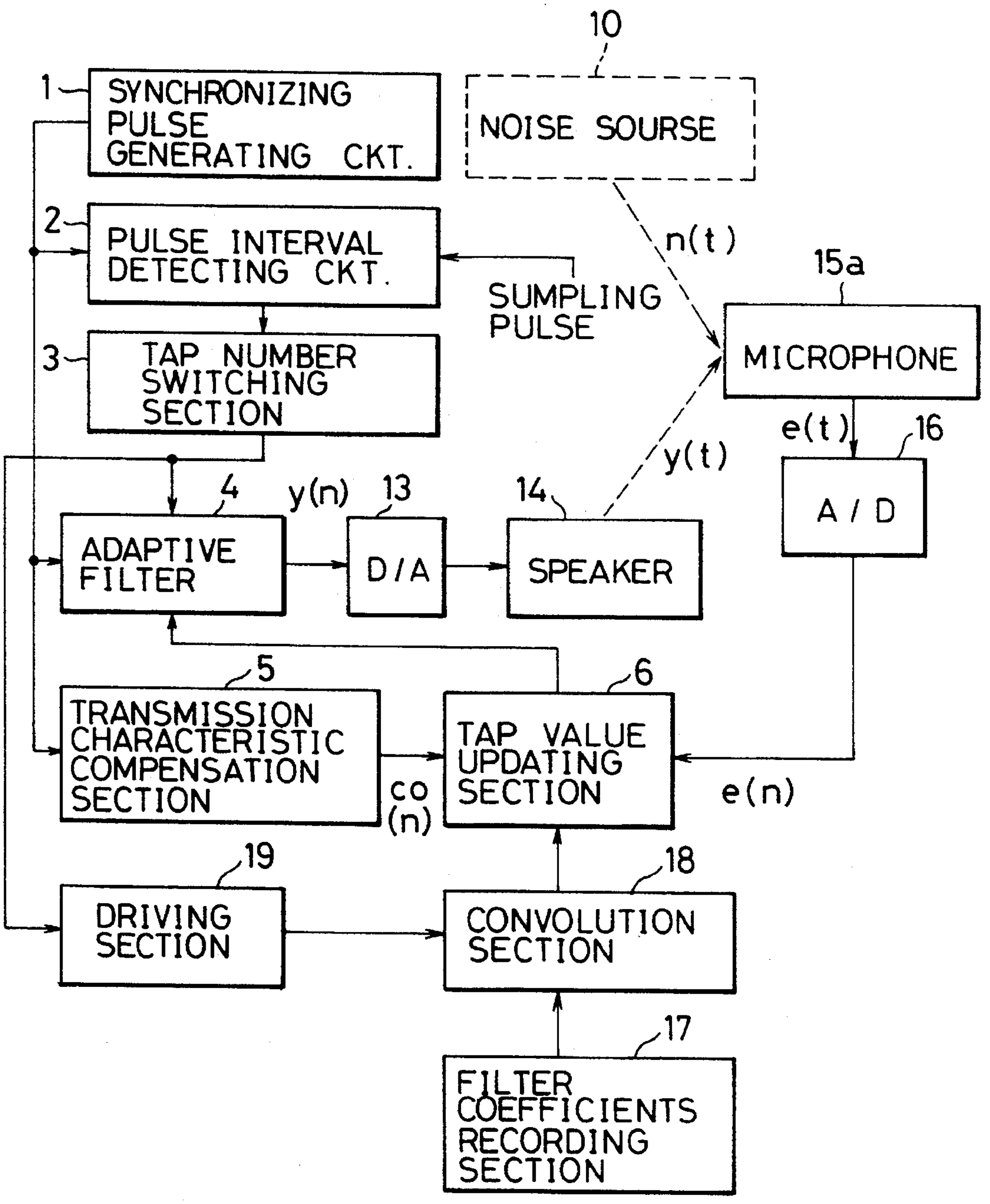
FIG. 1 is a block diagram showing an embodiment according to the present invention.

Referring now to FIG. 1, numeral 1 is a synchronizing pulse generating circuit for generating a pulse synchronized chronized with a period of a noise from a noise source 10. Numeral 2 is a pulse interval detecting circuit for detecting a pulse interval generated in the synchronizing pulse generating circuit 1. In this embodiment the pulse interval is detected by counting a pulse number of a sampling pulse of an A/D converter 16.

Numeral 3 is a tap number switching section for switching so as to equalize the tap number of the adaptive filter 4 with the number of the sampling pulse detected by pulse interval detecting circuit 2. Numeral 5 is a transmission section, characteristic compensation numeral 6 a tap value updating section, numeral 13 a D/A converter, numeral 14 a speaker, numeral 15 a microphone and numeral 16 an A/D converter.

Further, numeral 17 is a filter coefficient recording section for recording a filter coefficient to reduce a high frequency composition of a signal generated from the adaptive filter 4 and numeral 18 is a convolution section for convoluting the filter coefficient recorded in the filter coefficient recording section 17 into the tap value of the adaptive filter 4. Further, numeral 19 is a driver section for driving the convolution section 18.

In designing the system, the frequency of the sampling pulse is predetermined to be more than twice of the maximum frequency contained in signals outputted from the microphone 15.

For making explanations easier, the pulse width generated from the synthesizing pulse generating circuit 1 of the synthesizing pulse p (t) is defined to be 3 sampling times and the pulse interval detected by the pulse interval detecting circuit 2 is defined to be I samplings.

Figure 11:
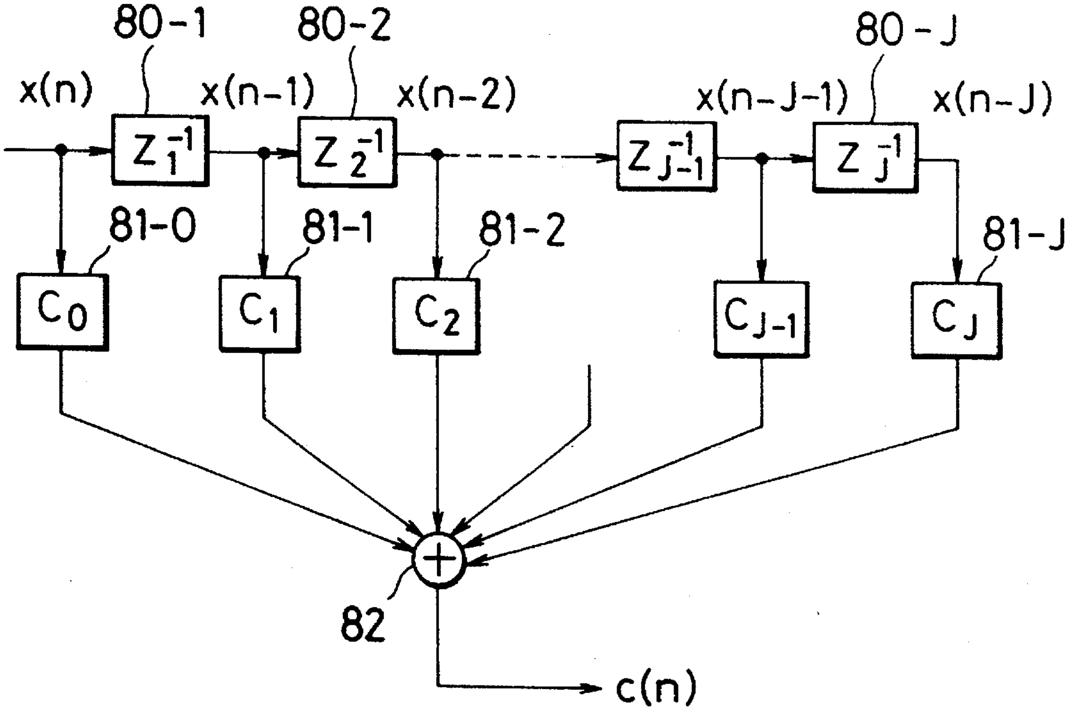
FIG. 11 is a diagram showing a transmission characteristic compensation section according to the prior art.

First, the transmission characteristic compensation section 5 will be described. The transmission characteristic compensation section 5 can be constituted like in FIG. 11 described before as an example of the prior art, however, by replacing an input signal of the noise source with a pulse signal it is possible to achieve a more simple construction. That is to say, when the pulse width x is normalized into "1", since only the coefficients existing in the delay element may be added, the formula (1) is:

$$C(n)=<i=k,\ k-2>\Sigma C_i \quad (6)$$

where k is a number of the delay element where the first input pulse exists.

Figure 3:
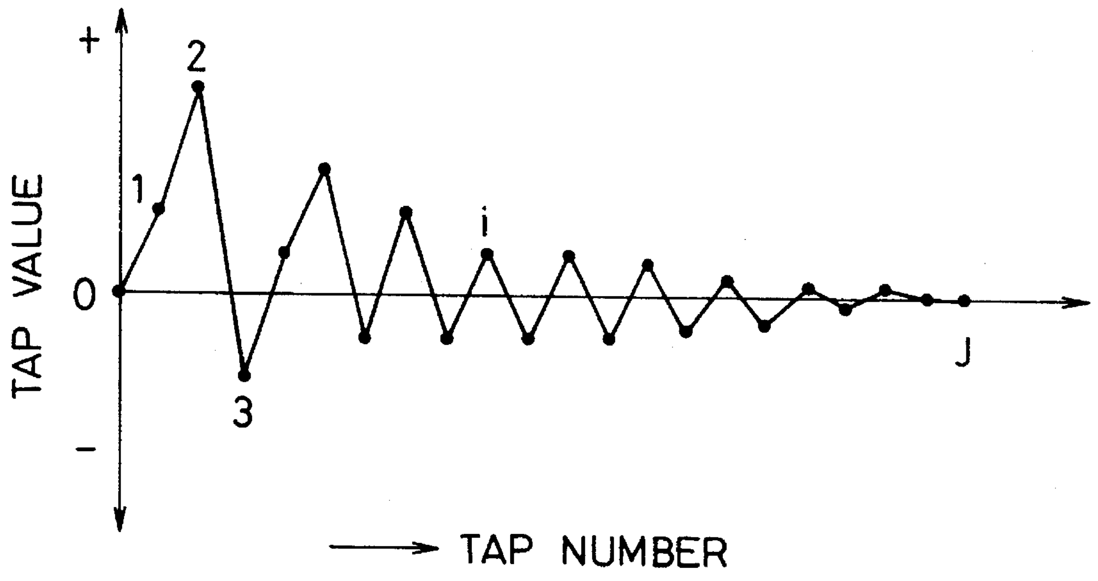
FIG. 3 is a diagram showing an example of a tap value of a transmission characteristic compensation section.

Further, the tap value $C_i$ as shown in FIG. 3 is determined if the position of the speaker 14, the position of the microphone 15 and the characteristic of the D/A converter 13 are determined. Therefore, when the first input pulse is a tap number k, the right side of the formula (6) is calculated beforehand and then the "k"th tap value CO (k) is:

$$CO(k)=<i=k,\ k-2>\Sigma C_i \quad (7)$$

where $C_i$=0if i<0and i>J.

Thus, an additional addition is not needed by memorizing the tap value at the memory of "k"th address.

Next, referring to FIG. 2, operations of the tap number switching section 3, the adaptive filter 4, the transmission characteristic compensation section 5 and the tap value updating section will be described.

The transmission characteristic compensation section 5 is composed of a memory 51 and in "k"th address of the memory, the value of CO (k) of the formula (7) is memorized.

The tap number switching section 3 is composed of a MOD (I) circuit 31. The tap value updating section 6 is composed of an address generating circuit 61, an adder 62, a MOD (I) circuit 63, and multiplication circuits 64 and 65. Further, the adaptive filter is composed of a counter 41, an address generating circuit 43, a memory 44 and an addition circuit 45. The counter 41 is reset by differentiating the pulse generated in the synthesizing pulse generating circuit 1 in a differential circuit 42 and then is repeated with a count value from 0 to I–1. The address generating circuit 43 generates the count value and address values of the count value –1 and –2 on time sharing. These three addresses correspond to $<i=K_1, K_2>$ of the formula (5).

The MOD (I) circuit 31 converts the data generated at the address generating circuit 43 into a modulus I and transmits it as an address of the memory 44. That is to say, in case where I is 30 for example, the MOD (I) outputs 0 the data value is 30, outputs 1 if the data value is 31, outputs –1 if the data value is 29, and outputs –2 if the data value is 28.

In the memory 44, the data value (tap value) corresponding to the address is read out, and is outputted after being added in the addition circuit 45. That is to say, in the addition circuit 45 an addition is conducted according to the formula (5) and then y (n) is outputted.

Figure 4:
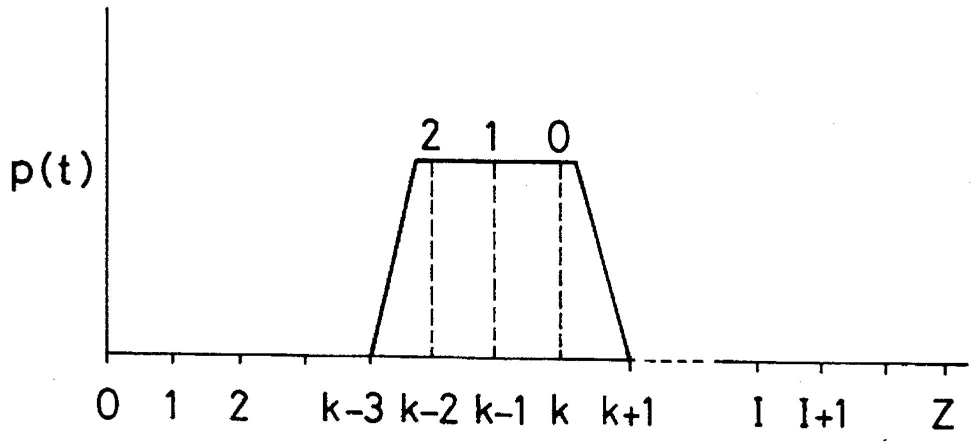
FIG. 4 is a graph showing a delay element with respect to a cyclic pulse p (t)
Figure 10:
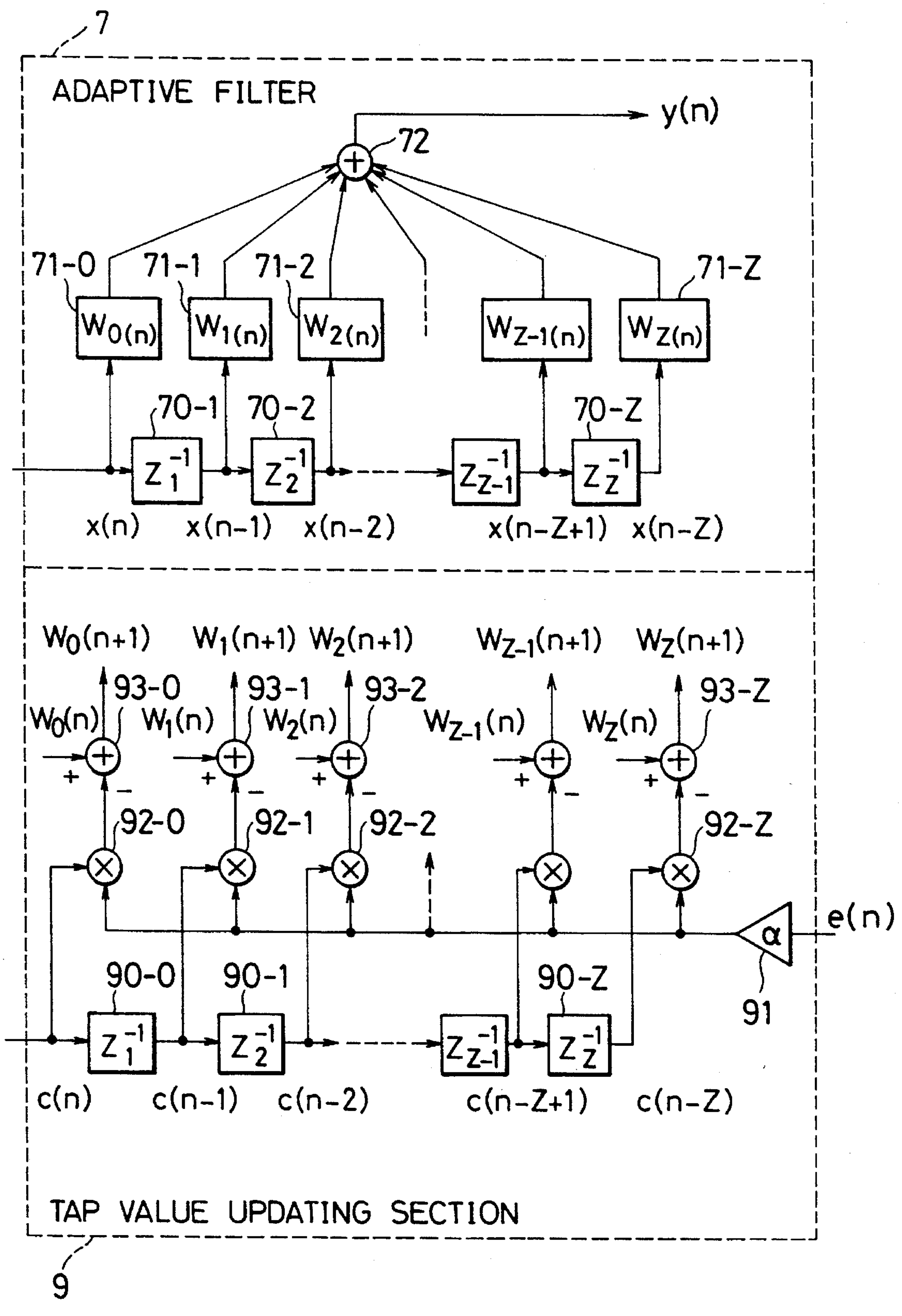
FIG. 10 is a diagram showing an adaptive filter and a tap value updating section according to the prior art.

Further explaining the calculation of the output value y (n) at the adaptive filter 4 according to an example of the prior art shown in FIG. 10, the synchronizing pulse p(t) is inputted from the synchronizing pulse generating circuit 1 to the delay element 70. FIG. 4 shows a state where the synchronizing pulse p (t) transmits the delay element 70. In the drawing the horizontal axis indicates element numbers and the vertical axis does a synchronizing pulse p (t) having three samplings width as defined before.

Figure 2:
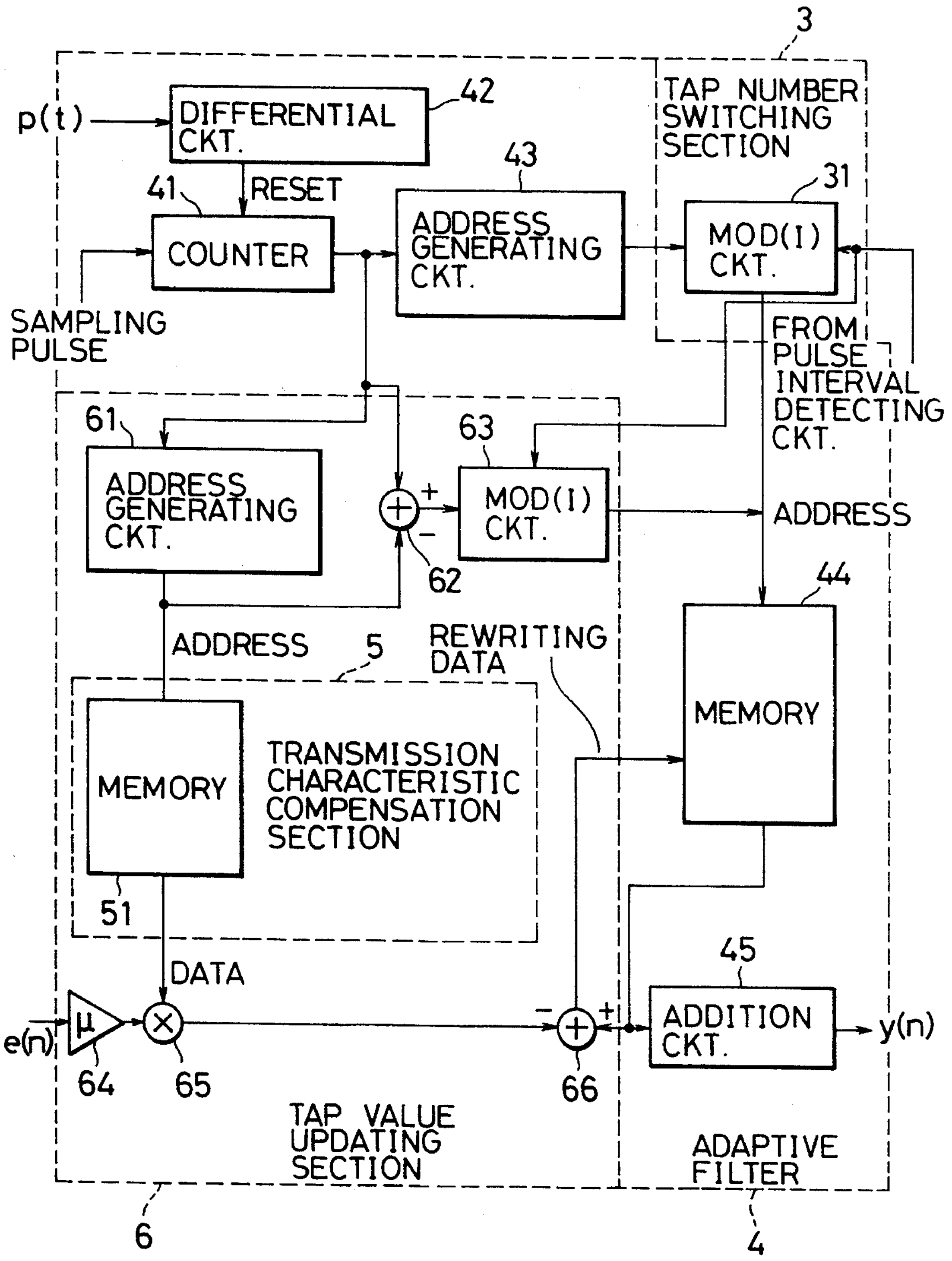
FIG. 2 is a schematic diagram showing an embodiment of a tap number switching section, an adaptive filter, a transmission characteristic compensation section, and a tap value updating section.

Further, the count value of the counter 41 as illustrated in FIG. 2 corresponds to the element number k existing in the first pulse of the synchronizing pulse p (t) as shown in FIG. 4. The address generating circuit 43 generates k, k–1 and k–2 based on k.

Figure 5:
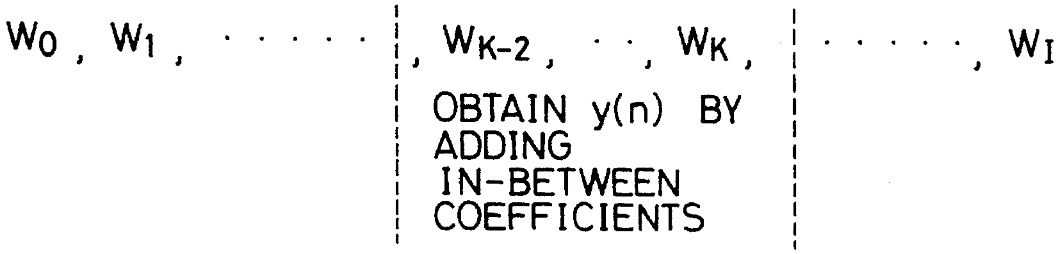
FIG. 5 is a drawing showing a calculation of an output value for an adaptive filter.

Consequently, as shown in FIG. 5, the output value y (n) outputted from the addition circuit 45 is formed by an addition of the tap value from $W_k$ to $W_{k-2}$ after terminating the calculation at $W_I$. When the addition circuit 45 finishes the calculation of y (n), the tap values stored in the memory 44 are started to be updated.

When the count value outputted from the counter 41 is changed, the address generating circuit 61 generates the address signals from 0 to J which correspond to k as indicated in the formula (7) with time sharing.

The transmission characteristic $HC_k$ is read out from the memory 51 by the address signal generated from the address generating circuit 61 and is inputted to the multiplier 65, whereby the output μ·e (n)·CO (k) is obtained.

On the other hand, the address signal generated from the address generating circuit 61 is reduced from the count value of the counter 41 in the adder 62 and inputted to the MOD (1) circuit 63. The output of the MOD (1) circuit 63 is supplied to the memory 44 as an address signal. Then therefrom the tap value $W_k$ (n) is read out and inputted to the addition circuit 66.

In the addition circuit 66, the tap value $W_k$ (n) is reduced by the output from the multiplication circuit 65.

$$W_k(n+1)=W_k(n)-\mu\cdot e(n)\cdot CO(K) \quad (9)$$

Namely, the tap value $W_k$ (n+1) has been stored into the memory 44 of the address k and thus the tap value has been updated.

Figure 6:
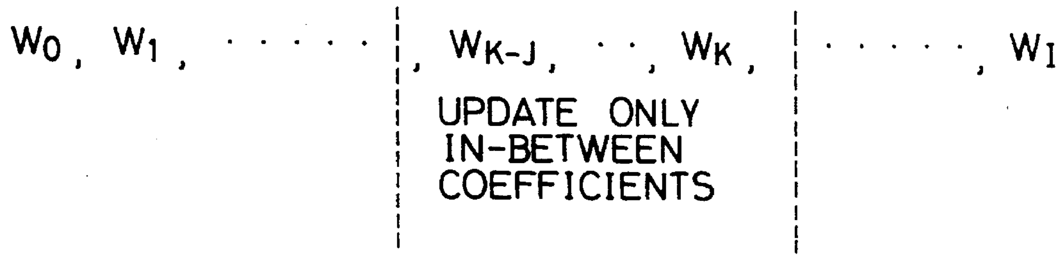
FIG. 6 is a drawing showing an updating of an adaptive filter.

With respect to the updating of the tap value, since the addresses from 0 to J are generated in the address generating circuit 61, where the count value of the counter 41 is k, the data in the memory 44 of the addresses corresponding to k to k−J are updated. That is to say, as shown in FIG. 6, the updatings from tap $W_k$ to $W_{k-J}$ of the adaptive filter are performed as illustrated in an example of the prior art of FIG. 10.

As described hereinbefore, by means of updating the tap value of the adaptive filter, the sound transmitted from the speaker 14 is able to have the same amplitude as and reversed phase to the noise sound from the noise source inputted to the microphone 15, thereby the noise sound nearby the microphone is attenuated.

The noise reduction system constituted above operates properly in case where the period of the noise sound from the noise source 10 is constant, however in case where the engine revolution is changed due to acceleration or deceleration of vehicle, there occurs a discontinuity in the signals outputted from the adaptive filter. Because of this discontinuity abnormal noises like "burble" are produced from the speaker 14. When the engine revolution is changed the period of noise is also changed, thereby the tap number I of the adaptive filter 4 is changed. When the tap number of the adaptive filter 4 is changed, individual tap value of the adaptive filter can not be updated so immediately into a tap value of the steady state, since it takes several times of updatings to reach a steady state. This is the reason why the discontinuity occurs when the engine revolution is changed.

In order to eliminate "burble" noises as mentioned above, there are provided a filter coefficients recording section 17, a convolution section 18 and a driving section 19 in the present invention.

Before explaining operations of these sections, a principle for eliminating these noises will be described first.

As described above, these "burble" noises occur when a tap number I of the adaptive filter 4 is changed. Consequently, it can be considered that these noises can be eliminated by inserting a filter to remove the high frequency component which causes these burble noises contained in the signals outputted from the adaptive filter 4.

Figure 8:
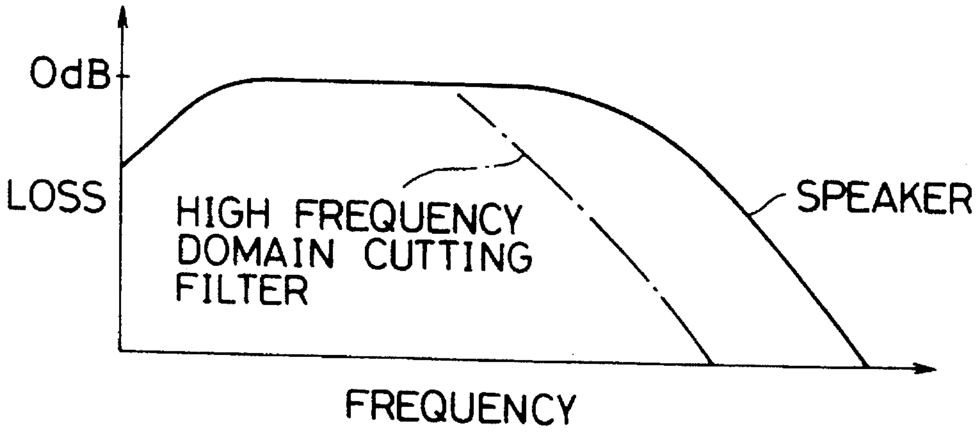
FIG. 8 is a drawing showing a function of a filter for convolution of an embodiment according to the present invention.
Figure 9:
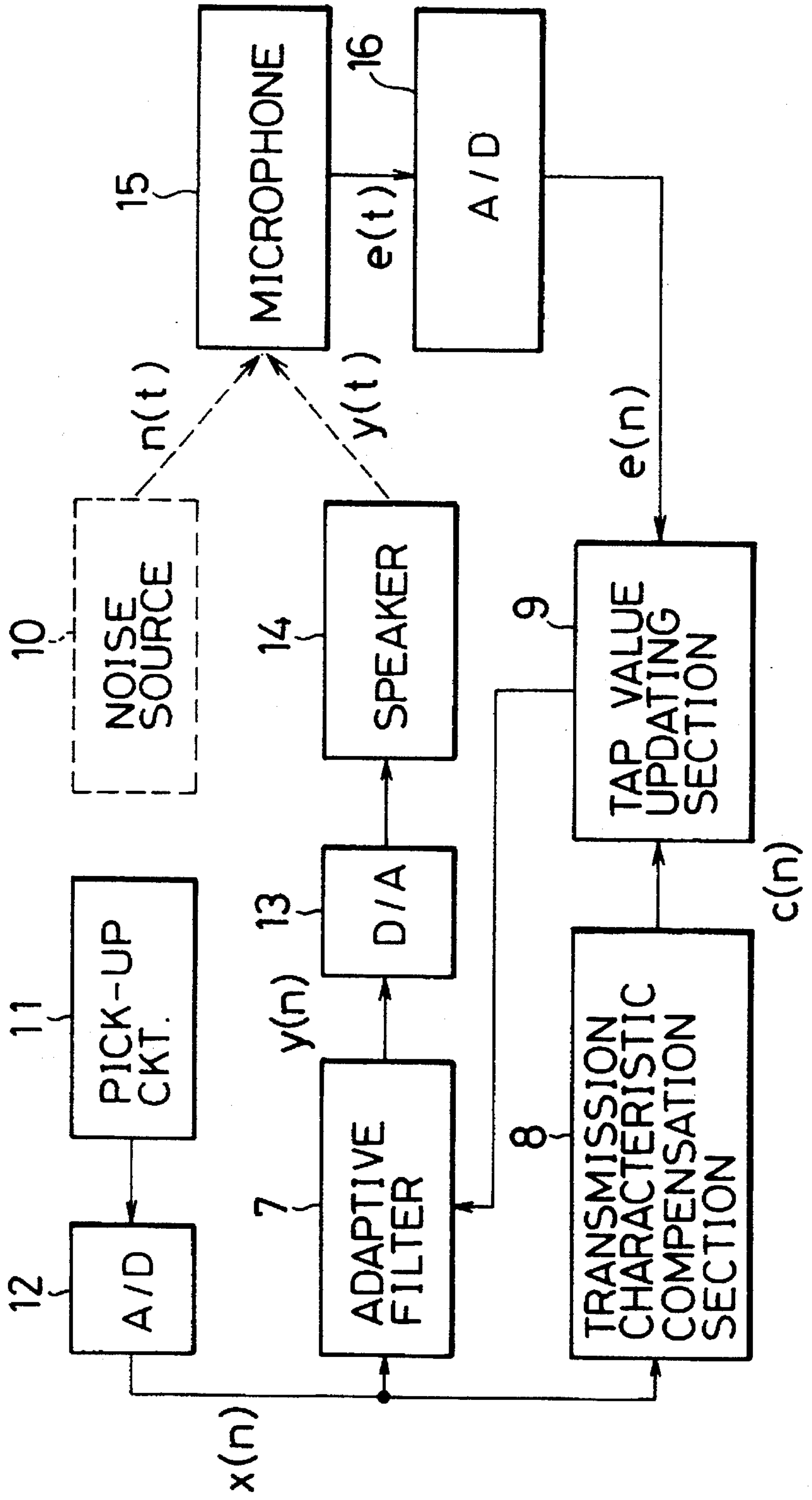
FIG. 9 is a schematic diagram showing a noise reduction system according to the prior art.

That is to say, such filter has a filter characteristic to cut a high frequency domain of the frequency characteristic for the speaker as illustrated in FIG. 8. On the other hand, inserting such filter for cutting the high frequency domain means at the same time that also the transmission characteristic of the transmission characteristic compensation section 5 must be changed. This induces a complicated construction of the system.

It is an idea of the present invention that the adaptive filter is used with a filter for cutting high frequency domains too. Namely, constituting two filters connected in series into one filter can be achieved by establishing a new filter coefficient by means of making a convolution process with each respective filter coefficient in these two filters.

For this purpose, filter coefficients of the filter for cutting the high frequency domain have been stored in the filter coefficients recording section 17. In the convolution section 18, the tap value of the adaptive filter 4 is established by convoluting a filter coefficient F recorded in the filter coefficients recording section 17 with a tap value formed in the tap value updating section 6 of the adaptive filter 4.

That is to say, the tap value $W_k$ (n+1) formed in the tap value updating section 6 according to the formula (9) is expressed as follows when the convolution is performed:

$$W_k(n+1)=\langle j=1,m\rangle \Sigma w_{t+j}(n+1)F_j \quad (10)$$

where m is a number of filter coefficient recorded in the filter coefficients recording section 17, t=k− (m+1)/2 (m is an odd number) . . . (11), and t=k−m / 2 (m is an even number) . . . (12)

Figure 7:
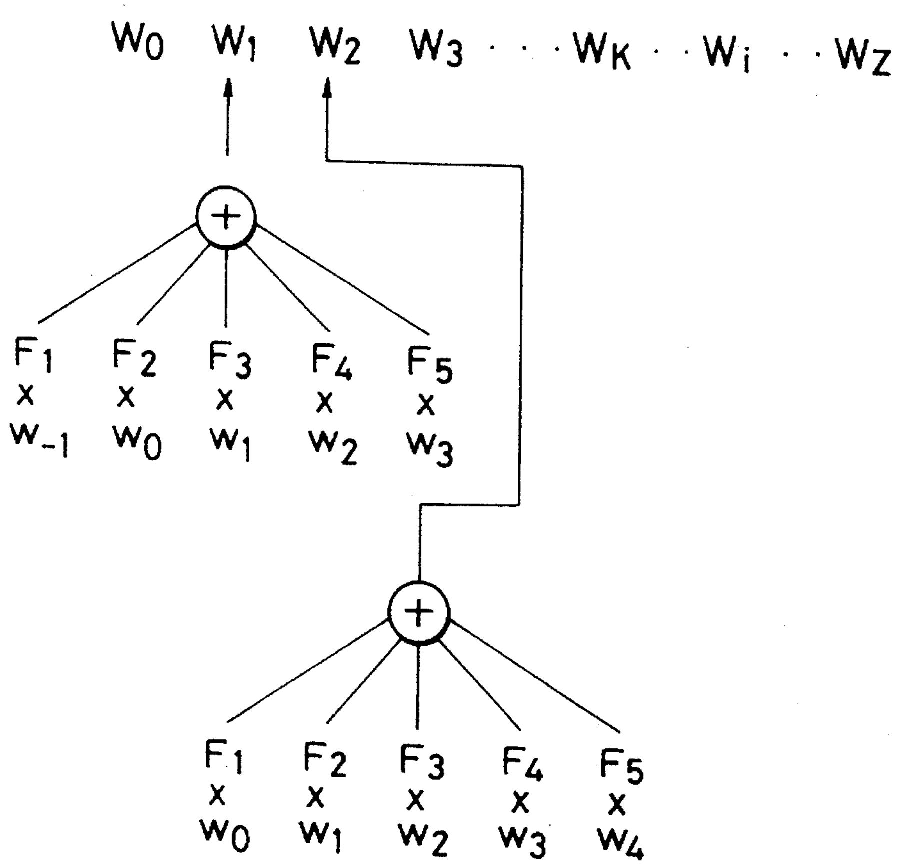
FIG. 7 is a drawing showing a convolution section of an embodiment according to the present invention.

The convolution process of the formula (10) in case of m=5 will be explained by referring to FIG. 7.

There exist tap values $W_0$ through $W_z$ in the adaptive filter 4 as shown in FIG. 10. Further, also there exist tap values $W_0$ through $W_z$ which are formed in the tap value updating section 6. Since m is 5, according to the formula (11) t is:

$$t=k-3$$

In case of k=1, according to the formula (10) $W_1$is:

$$W_1=w_{-1}F_1+w_0F_2+w_1F_3+w_2F_4+w_3F_5 \quad (13)$$

Similarly, in case of k=2, $W_2$ is:

$$W_2=w_0F_1+w_1F_2+w_2F_3+w_3F_4+w_4F5 \quad (14)$$

Since the value $w_{-1}$ in the formula (13) is not formed in the tap value updating section 6, the multiplication of this part may be neglected. FIG. 7 is an illustration showing the relationship between the formulas (13) and (14). Where $W_k$ is the tap value to be calculated, the multiplication of $w_k$ and the filter coefficient F is performed by setting the center of F at $F_{(m+1)/2}$ and then each result of multiplication with w is added.

Thus, by recording these tap values $W_k$ convoluted and newly formed in the memory 71 and operating them, the signal of the high frequency burble noise is cut and not outputted from the adaptive filter.

Further, the way of convolution of the adaptive filter is not limited to the way shown in this embodiment of the present invention.

The driver section 19 is for driving the convolution section 18 when the tap number I outputted from the tap number switching section 3 is changed. On the other hand, when it is judged that the tap number remains constant, the driver section 19 commands the convolution section 18 to discontinue the convolution.

In this embodiment the system is constituted such that the driver section is operated when the tap value is changed, however the system may be constituted such that the driver section is operated when the period of the noise sound from the sound source 10 is changed, that is to say, the pulse interval detected by the pulse interval detecting circuit 2 is changed.

Further, in this embodiment the system has one speaker and one microphone, however the principle can be applied to a noise reduction system having a plurality of speakers and microphones.

In summary, according to the present invention the pulse synthesized with the period of the noise sound is generated and inputted to the adaptive filter. On the other hand, the tap number of the delay line of the adaptive filter is terminated at the tap number which is equal to the interval of the inputted pulse, whereby the number of times for calculation at the adaptive filter can be substantially reduced and therefore the constitution of the system can be simplified.

Furthermore, in case where the tap number of the adaptive filter is changed according to the change of the period of the noise sound, the filter coefficient for cutting the high frequency domain is convoluted into the tap value of the adaptive filter, whereby noises caused by the change of the tap number can be eliminated even when the tap number of the adaptive filter is changed.

While the presently preferred embodiment of the present invention has been shown and described, it is to be understood that these disclosures are for the purpose of illustration and that various changes and modifications may be made without departing from the scope of the invention as set forth in the appended claims.

What is claimed is:

1. A vehicle internal noise reduction system for reducing an internal noise generated from a noise source having, an adaptive filter responsive to a noise signal picked up from said noise source for generating a canceling signal based on a tap number, a speaker responsive to said canceling signal for generating a canceling sound to cancel said internal noise in a passenger compartment, a microphone provided in said passenger compartment for receiving said internal noise and said canceling sound and for outputting an error signal as a result of a difference of said canceling sound and said internal noise, a transmission characteristic compensation section for generating a compensation signal to compensate a transmission characteristic of a propagation path between said adaptive filter and said microphone, and a tap value updating section for updating said tap value based on said compensation signal and said error signal and for transmitting said updated tap value to said adaptive filter, comprising:

synchronizing pulse generating means responsive to said noise signal for generating a synchronizing pulse synchronized with a period of said noise signal;

pulse interval detecting means for detecting an interval of said synchronizing pulse generated;

tap number switching means responsive to said interval for generating a cut-off number equal to a number of sampling pulses within said interval and for generating a signal of said cut-off number;

filter coefficients recording means for recording a filter coefficient to cut a specific frequency domain contained in said canceling signal;

convolution means for convoluting said filter coefficient into said tap value of said adaptive filter up to a number of times equal to said cut-off number and for outputting said convoluted tap value to said tap value updating section so as to shorten a number of times of calculations for convolution; and driver means responsive to said signal of said cut-off number for driving said convolution means each time when said period of said noise is changed.

2. The system according to claim 1, wherein said specific frequency domain includes at least a high frequency domain.

3. The system according to claim 1, wherein said convolution means include a calculation of sum of convolution products by coinciding a tap value to be calculated with a center value of said filter coefficients recorded in said filter coefficients recording means.

4. A vehicle internal noise reduction method for reducing an internal noise generated from a noise source having, an adaptive filter responsive to a noise signal picked up from said noise source for generating a canceling signal based on a tap number, a speaker responsive to said canceling signal for generating a canceling sound to cancel said internal noise in a passenger compartment, a microphone provided in said passenger compartment for receiving said internal noise and said canceling sound and for outputting an error signal as a result of a difference of said canceling sound and said internal noise, a transmission characteristic compensation section for generating a compensation signal to compensate a transmission characteristic of a propagation path between said adaptive filter and said microphone, and a tap value updating section for updating said tap value based on said compensation signal and said error signal and for transmitting said updated tap value to said adaptive filter, the method comprising:

generating a synchronizing pulse synchronized with a period of said noise signal;

detecting an interval of said synchronizing pulse generated;

generating a cut-off number equal to a number of sampling pulses within said interval and generating a signal of said cut-off number based on said interval;

recording a filter coefficient for cutting a specific frequency domain contained in said canceling signal;

convoluting said filter coefficient into said tap value of said adaptive filter up to a number of times equal to said cut-off number to thereby obtain a convoluted tap value and outputting said convoluted tap value to said tap value updating section so as to shorten the number of times of calculations for convolution; and, starting said calculations for convolution in response to said signal of said cut-off number each time when said period of said noise is changed.

* * * * *